(12) United States Patent
Chen et al.

(10) Patent No.: US 9,399,615 B2
(45) Date of Patent: Jul. 26, 2016

(54) CATALYST AND METHOD FOR HYDROGENATION OF 4,4'-METHYLENEDIANILINE

(71) Applicant: INDUSTRIAL TECHNOLOGY RESEARCH INSTITUTE, Hsinchu (TW)

(72) Inventors: Chao-Huang Chen, Hsinchu (TW); Chiou-Hwang Lee, Hsinchu (TW); Hsi-Yen Hsu, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/706,670

(22) Filed: May 7, 2015

(65) Prior Publication Data

US 2016/0152549 A1 Jun. 2, 2016

(30) Foreign Application Priority Data

Nov. 27, 2014  (TW) .............................. 103141126 A

(51) Int. Cl.
  *C07C 209/72* (2006.01)
  *B01J 23/58* (2006.01)

(52) U.S. Cl.
  CPC ............... *C07C 209/72* (2013.01); *B01J 23/58* (2013.01); *C07C 2101/14* (2013.01)

(58) Field of Classification Search
  None
  See application file for complete search history.

(56) References Cited

U.S. PATENT DOCUMENTS

| | | | |
|---|---|---|---|
| 232,389 A | 9/1880 | Burns | |
| 1,927,129 A | 9/1933 | Lommel et al. | |
| 2,092,525 A | 9/1937 | Adkins et al. | |
| 2,129,631 A | 9/1938 | Winans | |
| 2,511,028 A | 6/1950 | Whitman | |
| 2,606,924 A | 8/1952 | Whitman | |
| 2,606,925 A | 8/1952 | Whitman | |
| 2,606,927 A | 8/1952 | Barkdoll et al. | |
| 2,606,928 A | 8/1952 | Barkdoll et al. | |
| 3,155,724 A | 11/1964 | Arthur | |
| 3,347,917 A | 10/1967 | Arthur | |
| 3,591,635 A | 7/1971 | Farrissey, Jr. et al. | |
| 3,636,108 A | 1/1972 | Brake | |
| 3,644,522 A | 2/1972 | Brake et al. | |
| 3,676,495 A | 7/1972 | Hoeschele | |
| 3,697,449 A | 10/1972 | Brake | |
| 3,766,272 A | 10/1973 | Brake | |
| 3,825,586 A | 7/1974 | Traumann | |
| 3,856,862 A | 12/1974 | Chung et al. | |
| 3,914,307 A | 10/1975 | Massie | |
| 3,959,374 A | 5/1976 | Brennan et al. | |
| 4,161,492 A | 7/1979 | Weissel | |
| 4,186,145 A | 1/1980 | Weissel | |
| 4,394,522 A | 7/1983 | Allen | |
| 4,394,523 A | 7/1983 | Allen | |
| 4,448,995 A | 5/1984 | Allen | |
| 4,754,070 A | 6/1988 | Casey et al. | |
| 4,946,998 A | 8/1990 | Casey et al. | |
| 4,960,941 A | 10/1990 | Vedage et al. | |
| 5,026,914 A | 6/1991 | Jenkins et al. | |
| 5,196,594 A | 3/1993 | Schmelzer et al. | |
| 5,214,212 A | 5/1993 | Whitman | |
| 5,360,934 A | 11/1994 | Vedage et al. | |
| 5,545,756 A | 8/1996 | Vedage et al. | |
| 5,550,294 A | 8/1996 | Whitman | |
| 5,578,546 A | 11/1996 | Maschmeyer et al. | |
| 5,981,801 A | 11/1999 | Kim et al. | |
| 6,140,540 A | 10/2000 | Vedage et al. | |
| 6,184,416 B1 | 2/2001 | Ding et al. | |
| 6,998,507 B1 | 2/2006 | Ding et al. | |
| 7,038,088 B2 | 5/2006 | Ding et al. | |
| 7,304,183 B2 | 12/2007 | Su et al. | |
| 7,977,517 B2 | 7/2011 | Cortright et al. | |
| 8,017,818 B2 | 9/2011 | Cortright et al. | |
| 8,053,615 B2 | 11/2011 | Cortright et al. | |
| 8,350,108 B2 | 1/2013 | Cortright et al. | |
| 8,557,728 B2 | 10/2013 | Birdsall et al. | |
| 8,557,729 B2 | 10/2013 | Cairns et al. | |
| 8,563,460 B2 | 10/2013 | Birdsall et al. | |

(Continued)

FOREIGN PATENT DOCUMENTS

| CN | 1461746 A | 12/2003 |
|---|---|---|
| CN | 1646514 A | 7/2005 |

(Continued)

OTHER PUBLICATIONS

Du et al.,"Ruthenium Nanoparticles Loaded on Carbon as Effective Catalyst for Highly Selective Hydrogenation of 4,4'-Methylenedianiline", Chem. Res. Chinese Universities, 2012, 28(5), 882-885.

Kim et al.,"Ru-catalyzed hydrogenation of aromatic diamines: The effect of alkali metal salts", Journal of Molecular Catalysis A; Chemical 1998, 132, 267-276.

Wang et al., "Ru-catalyzed arene hydrogenation: a highly efficient and selective process for preparing trans-trans isomer of 4,4'-diamino-dicyclohexy", Advanced Materials Research vols. 393-395 (2012) pp. 1413-1416.

(Continued)

*Primary Examiner* — Sudhakar Katakam
*Assistant Examiner* — Jennifer C Sawyer
(74) *Attorney, Agent, or Firm* — Birch, Stewart, Kolasch & Birch, LLP

(57) ABSTRACT

Disclosed is a catalyst for hydrogenation of 4,4'-methylenedianiline (MDA), including a support, a magnesium-aluminum oxide layer covering the support, and a rhodium-ruthenium active layer loaded on the magnesium-aluminum oxide layer, wherein the rhodium and the ruthenium of the rhodium-ruthenium active layer have a weight ratio of 40:60 to 10:90. The hydrogenation catalyst can be collocated with hydrogen for hydrogenation of the MDA to form bis(para-amino cyclohexyl) methane (PACM), and the PACM contains 0 mol % to 25 mol % of (t,t)-isomer.

10 Claims, No Drawings

(56) References Cited

U.S. PATENT DOCUMENTS

| | | |
|---|---|---|
| 8,637,424 B2 | 1/2014 | Elsen |
| 8,722,922 B2 | 5/2014 | Chang et al. |
| 2002/0198409 A1 | 12/2002 | Bunnenberg et al. |
| 2004/0034252 A1 | 2/2004 | Stochniol et al. |
| 2005/0081443 A1 | 4/2005 | Aiello et al. |
| 2006/0052236 A1 | 3/2006 | Angevine et al. |
| 2006/0239893 A1 | 10/2006 | Zhang et al. |
| 2008/0216391 A1 | 9/2008 | Cortright et al. |
| 2008/0300434 A1 | 12/2008 | Cortright et al. |
| 2008/0300435 A1 | 12/2008 | Cortright et al. |
| 2010/0076233 A1 | 3/2010 | Cortright et al. |
| 2011/0166013 A1 | 7/2011 | Cairns et al. |
| 2011/0172086 A1 | 7/2011 | Birdsall et al. |
| 2011/0201494 A1 | 8/2011 | Birdsall et al. |
| 2011/0251431 A1 | 10/2011 | Hizaler Hoffmann et al. |
| 2012/0111768 A1 | 5/2012 | Elsen |
| 2012/0323041 A1 | 12/2012 | Hu et al. |
| 2013/0230721 A1 | 9/2013 | Coupland |

FOREIGN PATENT DOCUMENTS

| | | |
|---|---|---|
| CN | 1775353 A | 5/2006 |
| CN | 1313455 C | 5/2007 |
| CN | 101050184 A | 10/2007 |
| CN | 101966456 A | 2/2011 |
| CN | 102189001 A | 9/2011 |
| CN | 103265438 A | 8/2013 |
| EP | 0 324 190 A2 | 7/1989 |
| EP | 1 566 372 A2 | 8/2005 |
| TW | 461901 | 11/2001 |
| TW | 200300751 | 6/2003 |
| TW | 200301154 | 7/2003 |
| TW | 200403208 | 3/2004 |
| TW | 200418754 | 10/2004 |
| TW | 200427654 | 12/2004 |
| TW | I225505 | 12/2004 |
| TW | I229637 | 3/2005 |
| TW | I236931 | 8/2005 |
| TW | 200638988 | 11/2006 |
| TW | I273101 | 2/2007 |
| TW | 201012791 A1 | 4/2010 |
| TW | 201016809 A1 | 5/2010 |
| TW | 201121651 A1 | 7/2011 |
| TW | 201127913 A1 | 8/2011 |
| TW | 201134793 A1 | 10/2011 |
| TW | 201134794 A1 | 10/2011 |
| TW | 201136660 A1 | 11/2011 |
| TW | 201138198 A1 | 11/2011 |
| TW | I354690 B1 | 12/2011 |
| TW | I365765 | 6/2012 |
| TW | 201307439 A1 | 2/2013 |
| TW | 201315541 A1 | 4/2013 |
| TW | 201315712 A1 | 4/2013 |
| TW | 201323397 A1 | 6/2013 |
| TW | 201402453 A | 1/2014 |
| TW | I421240 B | 1/2014 |
| WO | WO 2004/007425 A2 | 1/2004 |

OTHER PUBLICATIONS

Wenting et al., "Experimental study on catalytic hydrogenation of MDA to prepare PACM containing lower trans-trans isomer", Huaxue Fanying Gongcheng Yu Gongyi, 2005, pp. 12, Chemical Reaction Engineering and Technology, vol. 21, No. 1, Feb. 2005, 12-15.

Taiwan Office Action dated Jun. 25, 2015 for Appl. No. 103141126.

CATALYST AND METHOD FOR HYDROGENATION OF 4,4'-METHYLENEDIANILINE

CROSS REFERENCE TO RELATED APPLICATIONS

The present application is based on, and claims priority from, Taiwan Application Serial Number 103141126, filed on Nov. 27, 2014, the disclosure of which is hereby incorporated by reference herein in its entirety.

TECHNICAL FIELD

The technical field relates to a hydrogenation of 4,4'-methylenedianiline, and in particular it relates to a catalyst for the hydrogenation.

BACKGROUND

Diamine compounds are important chemical raw materials, which may react with dianhydride to form polyimide (PI), or react with diacid to form a polyamide (PA) such as nylon, or react with carbonyl dichloride to form diisocyanate. The diisocyanate may further react with polyol to form polyurethane (PU). Bis(para-aminocyclohexyl) methane (PACM) is an important cycloaliphatic diamine, and its raw material includes 4,4'-methylenedianiline (MDA), wherein the benzene rings of the MDA can be completely hydrogenated to form the PACM. The hydrogenated product (PACM) includes three isomers: (cis,cis)-isomer (also known as (c,c)-isomer), (cis,trans)-isomer (also known as (c,t)-isomer), and (trans,trans)-isomer (also known as (t,t)-isomer). The molar ratio of the (t,t)-isomer in the PACM will influence the physical properties of the PACM. If the molar ratio of the (t,t)-isomer in the PACM is close to 50 mol % (balance composition), the PACM will be PACM-50. The PACM-50 has a high melting point, and is solid at room temperature under normal pressure. If the molar ratio of the (t,t)-isomer in the PACM is close to 20 mol % (balance composition), the PACM will be PACM-20. The PACM-20 has a low melting point, thereby being a liquid at room temperature. The major application of the PACM in early age is preparing nylon, such that high molar ratio of the (t,t)-isomer is beneficial in preparing transparent nylon. In other words, the PACM-50 is the mainstream of the production. However, the PACM-20 liquid has become mainstream in recent years because PACM-20 can be used to prepare diisocyanate liquid for the rapidly developing PU industry.

The diisocyanate prepared from the PACM raw material has excellent optical stability (anti-yellowing property), climate resistance, and mechanical properties, and is therefore suitable for preparing transparent polyamide resin, curing agent of epoxy resin, strong electrical insulator, raw material of magnetic binder, intermediate of dye, or medicine. Diisocyanate is widely applied in the optical, electronic, and medical fields, and the market for it is continuously increasing.

The hydrogenation of MDA for synthesizing PACM is developed and has been reported on many references, many years ago. Not only the reactivity and selectivity in the hydrogenation need to be included in consideration, but also the molar ratio of the isomer should be controlled. The design and development of the catalyst is critical in the hydrogenation of MDA. In recent years, patents have been continuously granted for novel catalysts. This means that the hydrogenation catalyst still needs to be modified. For example, a PACM product with a low (t,t)-isomer molar ratio prepared by hydrogenating the MDA at a high conversion rate is still called for.

SUMMARY

One embodiment of the disclosure provides a catalyst for hydrogenation of 4,4'-methylenedianiline, comprising: a support, a magnesium-aluminum oxide layer covering the support; and a rhodium-ruthenium active layer loaded on the magnesium-aluminum oxide layer, wherein the rhodium and the ruthenium of the rhodium-ruthenium active layer have a weight ratio of 40:60 to 10:90.

One embodiment of the disclosure provides a method of hydrogenating 4,4'-methylenedianiline, comprising: hydrogenating the 4,4'-methylenedianiline to form a bis(para-amino cyclohexyl) methane by the described catalyst with hydrogen.

A detailed description is given in the following embodiments.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

In one embodiment, the catalyst for hydrogenating MDA is provided. The catalyst includes a support and a magnesium-aluminum oxide layer covering the support. In one embodiment, the support can be silica, alumina, or another general porous support. In one embodiment, the support has a specific surface area of 100 $m^2/g$ to 300 $m^2/g$. In general, a greater specific surface area is more beneficial for hydrogenation. In one embodiment, the magnesium-aluminum oxide layer and the support have a weight ratio of 1:1 to 1:4. The magnesium and the aluminum of the magnesium-aluminum oxide layer have a weight ratio of 2:1 to 1:2. The magnesium content relates to the support properties (e.g. pH value). In general, the pH value of the support is enhanced by increasing the magnesium content. Appropriate magnesium content in the magnesium-aluminum oxide layer is beneficial for the reactivity and the product selectivity. In one embodiment, the magnesium-aluminum oxide layer can be formed as indicated below. Magnesium salt and aluminum salt are dissolved in an alkali solution to form a magnesium-aluminum sol-gel. The support and the magnesium-aluminum sol-gel are mixed and filtered to obtain a filtered cake. The filtered cake can be dried, sintered, and cracked to obtain the support with the surface covered with the magnesium-aluminum oxide layer.

The catalyst for hydrogenating MDA also includes a rhodium-ruthenium active layer loaded on the magnesium-aluminum oxide layer. In one embodiment, the rhodium and the ruthenium of the rhodium-ruthenium active layer have a weight ratio of 40:60 to 10:90. An active layer with an overly high ratio of ruthenium needs a higher reaction temperature and reaction pressure, thereby increasing the cost of equipment and safety. An active layer with an overly high ratio of rhodium will increase the catalyst cost and will not be favorable in commercialization. In one embodiment, the rhodium-ruthenium active layer and the support have a weight ratio of 1:24 to 1:16. An overly high ratio of the rhodium-ruthenium active layer will increase the catalyst cost. An overly low ratio of the rhodium-ruthenium active layer cannot efficiently hydrogenate the MDA.

In one embodiment, the catalyst is collocated with hydrogen to hydrogenate MDA to form PACM with a low molar ratio of (t,t)-isomer, as shown in Formula 1.

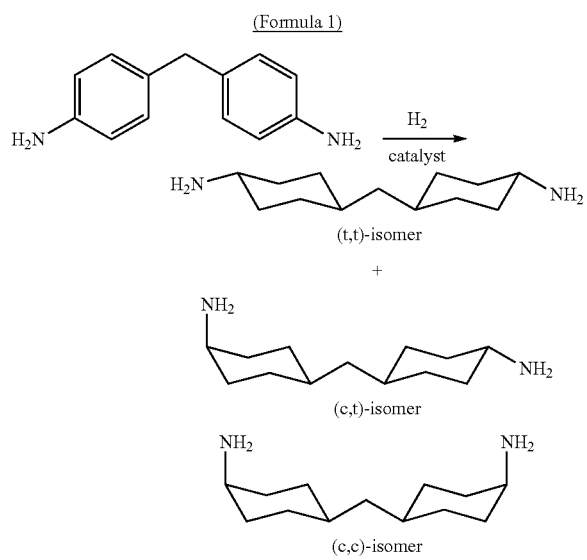

(Formula 1)

In one embodiment, the (t,t)-isomer occupies 25 mol % to 0 mol % of the PACM. An overly high content of the (t,t)-isomer in the PACM will make the PACM be solid rather than liquid at room temperature, it is unfavorable to the following application. The hydrogenation can be performed with a hydrogen pressure of 60 bar to 70 bar. In general, the hydrogenation rate is enhanced by increasing the hydrogen pressure, but an overly high hydrogen pressure also increases the cost of equipment and safety issue. In one embodiment, the hydrogenation is performed at a temperature of 120° C. to 160° C. The hydrogenation rate is enhanced by increasing the hydrogenation temperature, but an overly high temperature may increase the (t,t)-isomer content and the side product ratio of the product.

Below, exemplary embodiments will be described in detail so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1 (Preparation of the Catalysts)

Catalyst A was prepared according to simultaneous impregnation as described below. First, 1 L of an aqueous solution of de-ionized water, 256 g of magnesium nitrate, and 357 g of aluminum nitrate was added to 1 L of another aqueous solution of de-ionized water, 208 g of sodium hydroxide, and 152 g of sodium carbonate, and then stirred at room temperature to be aged for 18 hours to form a magnesium aluminum sol-gel. 200 g of alumina support was then added to the magnesium aluminum sol-gel, continuously stirred for 1 hour, and filtered to obtain a filtered cake. The filtered cake was washed with water 3 times, and then dried at 100° C. The dried filtered cake was cracked to a size of less than 100 mesh, thereby forming a powder of the alumina support with the surface covered with the magnesium-aluminum oxide layer. 15 g to 20 g of the powder was added to 60 g to 80 g of an impregnation solution, and then stirred for 40 minutes. The impregnation solution includes an aqueous solution of de-ionized water, ruthenium nitrosyl nitrate (Ru(NO)(NO$_3$)$_3$), and rhodium nitrate (Rh(NO$_3$)$_3$), wherein the ruthenium and rhodium concentrations correspond to desired ratios in the following Examples. The impregnated powder was filtered and dried, and then sintered at 450° C. for 4 hours to obtain the catalyst A.

Catalyst B was prepared according to sequential impregnation as described below. The powder of the alumina support with the surface covered with the magnesium-aluminum oxide layer was similar to that of the catalyst A. The difference for preparing the catalyst B was the impregnation solutions were ruthenium nitrosyl nitrate solution and rhodium nitrate solution, respectively, wherein the ruthenium and rhodium concentrations correspond to desired ratios in following Examples. The powder was first added to the impregnation solution of ruthenium nitrosyl nitrate, stirred for 40 minutes, filtered and dried at 110° C., then added to the impregnation solution of rhodium nitrate, stirred for 40 minutes, filtered and dried, and then sintered at 450° C. for 4 hours to obtain the catalyst B.

Catalyst C was prepared according to the incipient wetness method described below. The powder of the alumina support with the surface covered with the magnesium-aluminum oxide layer was similar to that of the catalyst A. The metal precursors were ruthenium nitrosyl nitrate and rhodium nitrate, too. The difference of the catalyst C and the catalyst A was that the catalyst C was prepared according to the incipient wetness method rather than the impregnation. In the incipient wetness method, an appropriate amount of the metal precursor solution was slowly and dropwise added to the powder, wherein the powder was simultaneously stirred. After the metal precursor solution was completely added to the powder, the powder surface was slightly wet. As such, the solution amount was the appropriate amount for the incipient wetness method. The wet powder was dried and then sintered at 450° C. for 4 hours to obtain the catalyst C.

Example 2

7 mL of the catalyst A with a size of 20-30 mesh was prepared, which contained 4.5 wt % of Ru and 0.5 wt % of Rh. The catalyst was put in a fixed bed reactor and tested by a continuous trickle-bed mode. MDA85 (containing 85 mol % MDA and 15 mol % high cyclic oligomer, commercially available from Shuang-bang Ind. Corp.) was hydrogenated in the above reactor with hydrogen. The hydrogenation factors are listed below: the solvent was THF, the MDA85 concentration of the THF solution was 25 wt %, the weight hourly space velocity (WHSV) of the THF solution was 0.26 hr$^{-1}$, the hydrogenation temperature was 140° C., the hydrogenation pressure was 70 kg/cm$^2$, and the hydrogen and the MDA had a molar ratio of 69:1. The hydrogenation result was analyzed by gas chromatography (GC) as indicated below: the MDA conversion ratio was 100% without any monocyclic hydrogenated intermediate H$_6$MDA, the PACM selectivity was 92.6%, and the (t,t)-isomer of the PACM product was 22.3 mol %.

Example 3

7 mL of the catalyst A with a size of 20-30 mesh was prepared, which contained 3 wt % of Ru and 2 wt % of Rh.

The catalyst was put in a fixed bed reactor and tested by a continuous trickle-bed mode. MDA85 was hydrogenated in the above reactor with hydrogen. The hydrogenation factors are listed below: the solvent was THF, the MDA85 concentration of the THF solution was 25 wt %, the WHSV of the THF solution was 0.25 hr$^{-1}$, the hydrogenation temperature was 130° C., the hydrogenation pressure was 70 kg/cm$^2$, and the hydrogen and the MDA had a molar ratio of 60:1. The hydrogenation result was analyzed by GC as shown below: the MDA conversion ratio was 100% without any H$_6$MDA, the PACM selectivity was 94.0%, and the (t,t)-isomer of the PACM product was 15.9 mol %.

Example 4

7 mL of the catalyst A with a size of 20-30 mesh was prepared, which contained 4 wt % of Ru and 1 wt % of Rh. The catalyst was put in a fixed bed reactor and tested by a continuous trickle-bed mode. MDA85 was hydrogenated in the above reactor with hydrogen. The hydrogenation factors are listed below: the solvent was THF, the MDA85 concentration of the THF solution was 30 wt %, the WHSV of the THF solution was 0.43 hr$^{-1}$, the hydrogenation temperature was 140° C., the hydrogenation pressure was 70 kg/cm$^2$, and the hydrogen and the MDA had a molar ratio of 34:1. The hydrogenation result was analyzed by GC as summarized below: the MDA conversion ratio was 100% without any H$_6$MDA, the PACM selectivity was 94.9%, and the (t,t)-isomer of the PACM product was 18.8 mol %. After the hydrogenation was performed for about 1000 hours, wherein the WHSV was 0.28 hr$^{-1}$ to 0.43 hr$^{-1}$ and the hydrogen and the MDA had a molar ratio of 34:1 to 52:1, the product contained 1 mol % to 3 mol % of H$_6$MDA. The occurrence of the H$_6$MDA means that the catalyst activity reduced.

Example 5

7 mL of the catalyst B with a size of 20-30 mesh was prepared, which contained 4 wt % of Ru and 1 wt % of Rh. The catalyst was put in a fixed bed reactor and tested by a continuous trickle-bed mode. MDA85 was hydrogenated in the above reactor with hydrogen. The hydrogenation factors are listed below: the solvent was THF, the MDA85 concentration of the THF solution was 25 wt %, the WHSV of the THF solution was 0.27 hr$^{-1}$, the hydrogenation temperature was 140° C., the hydrogenation pressure was 70 kg/cm$^2$, and the hydrogen and the MDA had a molar ratio of 53:1. The hydrogenation result was analyzed by GC as illustrated below: the MDA conversion ratio was 100% without any H$_6$MDA, the PACM selectivity was 93.3%, and the (t,t)-isomer of the PACM product was 22.8 mol %.

Example 6

7 mL of the catalyst B with a size of 20-30 mesh was prepared, which contained 4 wt % of Ru and 1 wt % of Rh. The catalyst was put in a fixed bed reactor and tested by a continuous trickle-bed mode.MDA100 (containing 100 mol % MDA, commercially available from Shuang-bang Ind. Corp.) was hydrogenated in the above reactor with hydrogen. The hydrogenation factors are listed below: the solvent was THF, the MDA100 concentration of the THF solution was 25 wt %, the WHSV of the THF solution was 0.35 hr$^{-1}$, the hydrogenation temperature was 130° C., the hydrogenation pressure was 70 kg/cm$^2$, and the hydrogen and the MDA had a molar ratio of 42:1. The hydrogenation result was analyzed by GC as shown below: the MDA conversion ratio was 100% without any H$_6$MDA, the PACM selectivity was 93.5%, and the (t,t)-isomer of the PACM product was 17.0 mol %.

Example 7

13.5 mL of the catalyst C with a size of 20-30 mesh was prepared, which contained 4 wt % of Ru and 1 wt % of Rh. The catalyst was put in a fixed bed reactor and tested by a continuous trickle-bed mode. MDA85 was hydrogenated in the above reactor with hydrogen. The hydrogenation factors are listed below: the solvent was THF, the MDA85 concentration of the THF solution was 25 wt %, the WHSV of the THF solution was 0.27 hr$^{-1}$, the hydrogenation temperature was 140° C., the hydrogenation pressure was 70 kg/cm$^2$, and the hydrogen and the MDA had a molar ratio of 51:1. The hydrogenation result was analyzed by GC as illustrated below: the MDA conversion ratio was 100% without any H$_6$MDA, the PACM selectivity was 92.0%, and the (t,t)-isomer of the PACM product was 20.3 mol %.

Example 8

2.5 g of the catalyst A was prepared, which contained 5 wt % of Rh. The catalyst A, 50 g of MDA85, and 75 g of THF were put in an autoclave reactor for hydrogenation. The hydrogenation factors are listed below: the hydrogenation temperature was 160° C., the hydrogenation pressure was 60 kg/cm$^2$, the hydrogenation was stopped when the hydrogen pressure was not changed, and the hydrogenation period was 210 minutes. The hydrogenation result was analyzed by GC as indicated below: the MDA conversion ratio was 100% without any H$_6$MDA, the PACM selectivity was 93.7%, and the (t,t)-isomer of the PACM product was 25.0 mol %. Accordingly, the rhodium catalyst loaded on the support with the surface covered by the magnesium-aluminum oxide layer may tune the reaction activity to simultaneously achieve high reactivity, high selectivity, and low molar ratio of the (t,t)-isomer in the PACM product.

Example 9

2.5 g of a powder catalyst of 5 wt % of Rh loaded on Al$_2$O$_3$ support (commercially available from Alfa Aesar), 50 g of MDA85, 75 g of THF, and 0.125 g of LiOH were put in an autoclave reactor for hydrogenation. The hydrogenation factors are listed below: the hydrogenation temperature was 160° C., the hydrogenation pressure was 60 kg/cm$^2$, the hydrogenation was stopped when the hydrogen pressure was not changed, and the hydrogenation period was 60 to 120 minutes. The hydrogenation result was analyzed by GC as shown below: the MDA conversion ratio was 100% without any H$_6$MDA, the PACM selectivity was 65%, and the (t,t)-isomer of the PACM product was 39.0 mol %. Accordingly, the rhodium catalyst loaded on the support with the surface not covered by the magnesium-aluminum oxide layer has a low selectivity and high molar ratio of the (t,t)-isomer in the PACM product.

Example 10

2.5 g of a powder catalyst of 5 wt % of Ru loaded on Al$_2$O$_3$ support (commercially available from Alfa Aesar), 50 g of MDA85, 75 g of THF, and 0.125 g of LiOH were put in an autoclave reactor for hydrogenation. The hydrogenation factors are listed below: the hydrogenation temperature was 160° C., the hydrogenation pressure was 60 kg/cm$^2$, the hydrogenation was stopped when the hydrogen pressure was not changed, and the hydrogenation period was 420 minutes. The hydrogenation result was analyzed by GC as shown below: the MDA conversion ratio was about 100%, the PACM selectivity was 91.1%, and the (t,t)-isomer of the PACM product was 43.5 mol %. Accordingly, the commercially available ruthenium catalyst has low reaction activity (and therefore a long hydrogenation period), and high molar ratio of the (t,t)-isomer in the PACM product (>25 mol %).

Example 11

2.5 g of a powder catalyst of 5 wt % of Rh loaded on $LiAl_5O_8$ (prepared by incipient wetness method, and the support was prepared by Example 7 in U.S. Pat. No. 5,885,917), 50 g of MDA85, 75 g of THF, and 0.125 g of LiOH were put in an autoclave reactor for hydrogenation. The hydrogenation factors are listed below: the hydrogenation temperature was 160° C., the hydrogenation pressure was 60 kg/cm$^2$, the hydrogenation was stopped when the hydrogen pressure was not changed, and the hydrogenation period was 210 minutes. The hydrogenation result was analyzed by GC as shown below: the MDA conversion ratio was about 100%, the PACM selectivity was 89.4%, and the (t,t)-isomer of the PACM product was 48.0 mol %. Compared to the rhodium catalyst loaded on the alumina support covered with the magnesium-aluminum oxide layer, the rhodium catalyst loaded on the alumina support with the surface modified by lithium could not efficiently enhance the selectivity nor efficiently decrease the molar ratio of the (t,t)-isomer in the PACM product.

Example 12

4 wt % of Ru and 1 wt % of Rh were loaded on alumina support by incipient wetness method, and the support was commercially available from UOP. 7 mL of the catalyst was put in a fixed bed reactor and tested by a continuous trickle-bed mode. MDA85 was hydrogenated in the above reactor with hydrogen. The hydrogenation factors are listed below: the solvent was THF, the MDA85 concentration of the THF solution was 25 wt %, the WHSV of the THF solution was 0.22 hr$^{-1}$, the hydrogenation temperature was 140° C., the hydrogenation pressure was 70 kg/cm$^2$, and the hydrogen and the MDA had a molar ratio of 41:1. After the hydrogenation was performed for about 140 hours, the product contained $H_6MDA$. Accordingly, the activity of the catalyst loaded on the alumina support with the surface not covered with the magnesium-aluminum oxide layer was easily reduced.

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:

1. A catalyst for hydrogenation of 4,4'-methylenedianiline, comprising:
    a support,
    a magnesium-aluminum oxide layer covering the support; and
    a rhodium-ruthenium active layer loaded on the magnesium-aluminum oxide layer,
    wherein the rhodium and the ruthenium of the rhodium-ruthenium active layer have a weight ratio of 40:60 to 10:90.

2. The catalyst as claimed in claim 1, wherein the support comprises silica or alumina.

3. The catalyst as claimed in claim 1, wherein the support has a specific surface area of 100 m$^2$/g to 300 m$^2$/g.

4. The catalyst as claimed in claim 1, wherein the magnesium-aluminum oxide layer and the support have a weight ratio of 1:1 to 1:4.

5. The catalyst as claimed in claim 1, wherein the magnesium and the aluminum of the magnesium-aluminum oxide layer have a weight ratio of 2:1 to 1:2.

6. The catalyst as claimed in claim 1, wherein the rhodium-ruthenium active layer and the support have a weight ratio of 1:24 to 1:16.

7. A method of hydrogenating 4,4'-methylenedianiline, comprising:
    hydrogenating the 4,4' -methylenedianiline to form a bis (para-amino cyclohexyl) methane by the catalyst as claimed in claim 1 with hydrogen.

8. The method as claimed in claim 7, wherein the bis(para-amino cyclohexyl) methane has a t,t-isomer molar ratio of 25 mole % to 0 mole %.

9. The method as claimed in claim 7, wherein the hydrogen has a pressure of 60 bar to 70 bar.

10. The method as claimed in claim 7, wherein the step of hydrogenating the 4,4'-methylenedianiline is performed at a temperature of 120° C. to 160° C.

* * * * *